United States Patent
Loscutoff et al.

(10) Patent No.: US 12,106,835 B2
(45) Date of Patent: Oct. 1, 2024

(54) RELATING DATA TO IDENTIFIERS FOR VARIANT TESTING

(71) Applicant: Clover Health, Jersey City, NJ (US)

(72) Inventors: Peter Vladimir Loscutoff, Berkeley, CA (US); Jasmine Tsai, Jersey City, NJ (US)

(73) Assignee: Clover Health, Jersey City, NJ (US)

( * ) Notice: Subject to any disclaimer, the term of this patent is extended or adjusted under 35 U.S.C. 154(b) by 488 days.

(21) Appl. No.: 16/167,343

(22) Filed: Oct. 22, 2018

(65) Prior Publication Data

US 2020/0126650 A1    Apr. 23, 2020

(51) Int. Cl.
| | |
|---|---|
| *G16H 20/00* | (2018.01) |
| *G16H 50/20* | (2018.01) |
| *G16H 50/30* | (2018.01) |
| *G16H 80/00* | (2018.01) |
| *G06N 20/00* | (2019.01) |

(52) U.S. Cl.
CPC ............ *G16H 20/00* (2018.01); *G16H 50/20* (2018.01); *G16H 50/30* (2018.01); *G16H 80/00* (2018.01); *G06N 20/00* (2019.01)

(58) Field of Classification Search
None
See application file for complete search history.

(56) References Cited

U.S. PATENT DOCUMENTS

| | | | |
|---|---|---|---|
| 7,912,842 B1 | 3/2011 | Bayliss | |
| 2002/0123906 A1* | 9/2002 | Goetzke | G16H 50/20 |
| | | | 705/2 |
| 2006/0155581 A1 | 7/2006 | Eisenberger et al. | |
| 2007/0260492 A1* | 11/2007 | Feied | G16H 50/70 |
| | | | 705/3 |
| 2008/0082356 A1* | 4/2008 | Friedlander | G16H 10/60 |
| | | | 702/19 |
| 2015/0006587 A1 | 1/2015 | Segaran | |
| 2015/0205827 A1 | 7/2015 | Sengupta et al. | |

(Continued)

FOREIGN PATENT DOCUMENTS

CN    106471506 A  *  3/2017  ......... G06F 21/6245

OTHER PUBLICATIONS

Amy Gallo, "A Refresher on A/B Testing", retrieved on Dec. 12, 2019 at <<https://hbr.org/2017/06/a-refresher-on-ab-testing>>, Jun. 28, 2017, 9 pages.

(Continued)

*Primary Examiner* — Lena Najarian
(74) *Attorney, Agent, or Firm* — Lee & Hayes, P.C.

(57) ABSTRACT

Systems and methods for identifying related data for variant testing are disclosed. For example, data stored for records from disparate data sources may not include the same identifiers for all records such that it may not be readily identified as record for the same member. The presently-disclosed systems and methods generate data tagged as identifier information and determine the degree of similarity between the identifier information. Based at least in part on the degree of similarity meeting or exceeding a threshold amount of similarity, the data may be associated with a member identifier. By properly identifying user information corresponding to member identifiers, the members may be split in meaningful ways to perform variant test.

19 Claims, 6 Drawing Sheets

(56) References Cited

U.S. PATENT DOCUMENTS

| | | | | |
|---|---|---|---|---|
| 2015/0236849 A1* | 8/2015 | Ayday | ............... | H04L 9/0819 |
| | | | | 713/193 |
| 2015/0254308 A1* | 9/2015 | Scott | ............. | G06F 16/23 |
| | | | | 707/780 |
| 2016/0189201 A1* | 6/2016 | Shao | ............ | G06Q 30/0243 |
| | | | | 705/14.42 |
| 2017/0053002 A1 | 2/2017 | Bowman et al. | | |
| 2017/0124216 A1* | 5/2017 | Miller | ............. | G16H 10/60 |
| 2017/0316432 A1* | 11/2017 | Xu | ............. | G06F 3/0484 |

OTHER PUBLICATIONS

Gliklich, et al, "Registries for evaluating patient outcomes: a user's guide", retrieved on Dec. 12, 2019 at <<https:1/effectivehealthcare.ahrq.gov/sites/defau1Ufiles/pdf/registries-guide-3rd-edition_research.pdf>>, Apr. 2014, 89 pages.

PCT Search Report & Written Opinion for Application No. PCT/US2019/057223, mailed on Jan. 10, 2020, 14 pgs.

\* cited by examiner

RELATING DATA TO IDENTIFIERS FOR VARIANT TESTING

BACKGROUND

Data from disparate sources may be aggregated and used. In some instances, identifying related data from disparate sources may be difficult due to the data having different identifier formats. Means to identify related data having different identifier formats may be desired. Described herein are improvements in technology and solutions to technical problems that can be used to, among other things, identify and aggregate related data having different identifier formats.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

DETAILED DESCRIPTION

Systems and methods for relating data from disparate sources to identifiers are described herein. Take, for example, a network of systems that store or otherwise access stored data associated with users. Each system in the network may utilize its own data to, for example, identify a user for the system. The network of systems may wish to aggregate user data such that a given system may use its own data as well as data from other systems to have more data on the user and to better understand and serve the user. However, in examples, data sharing between systems may be difficult because the user information and identifier format may be inconsistent across systems. For instance, a user may be identified by a number of identifier types (e.g., name, surname, address, user identifier (ID), SSN, etc.). Each system may use a different combination of identifier types and may also assign their own user ID. In an example, the user ID assigned by the system may change if the user is disenrolled and reenrolled. Additionally, given time, the identifier information such as last name or address for the same user may change. In these and other examples, the need arises to match the user data from the network of systems to persistent member identifiers without allowing participating systems to change the member identifiers.

The present innovation is directed to systems and methods that generates persistent member identifiers and utilizes identifier matching algorithms to match data from disparate sources to the persistent member identifiers in a way that allows participating systems to perform meaningful variant testing without leakage. For example, the network of systems may be a service provider network that stores and/or has access to health-related information of its members. The service provider network may be interested in running an AB test to enhance a certain health-related outcome, such as, for example, a likelihood that a member will adhere to a medication plan. The AB test may be controlled experiment having two-samples for hypothesis testing and is a way to compare two versions of a test by randomly assigning the test group to one of the two versions of the test, measuring response to variable A against variable B, and determining which of the two variables is more effective.

In the example utilized above, the first service provider may have access to health-related data associated with network members utilizing their service and the second service provider may have access to different health-related data associated with network members that utilize their service. On their own, the first service provider and the second service provider could utilize their own data to assign one of two versions of the AB test to enhance the likelihood that a given member and/or set of members will adhere to a medication plan. However, if the service provider network was able to utilize all data within the network, the data sample size would increase and/or different categories of data (e.g., age, medical conditions, living conditions, etc.) would be available to the network, which may increase the accuracy of the test. Additionally, by identifying which data belongs to which network member, this could prevent leakage between the groups that are assigned one of two versions of the AB test. That is, this could prevent accidently assigning the same member, who may be identified as two different members based on the data from first service provider and the second service provider, to two versions of the same AB test.

It is to be appreciated that, over time, the amount of customer data maintained by such a network of systems, or service provider network, can become quite large as the number of users increases, and as the amount of records generated on behalf of these users increase merely by using the service provider network. With the availability of this vast collection of user data, an identifier matching algorithm may be leveraged to classify new data to correspond to member identifiers.

The systems described herein may perform identifier matching by receiving data tagged as identifier information and cross-referencing other tagged identifier information from other records to find overlaps or degrees of similarity. Based at least in part on a sufficient degree of similarity, the identifier matching algorithm can be used to match identifier information in new records to an existing member identifier and the data in the new records may also be automatically aggregated with data already associated with this existing member identifier. Otherwise, the identifier matching algorithm can determine to generate a new member identifier and associate data in the new records to the new member identifier. That is, upon receiving new data, the system may automatically match the data to a member identifier and may automatically aggregate the data for the member. By automatically aggregating the data for members, the service provider wishing to identify members for health interventions or other variant tests of interest may setup rules to be automatically notified when members meeting certain data criteria are identified.

Implementations of the techniques and systems described herein can improve existing technologies (e.g., record management technologies), and can improve the functioning of the systems with respect to conventional systems. In particular, the implementations described herein allow a record management system to identify a specific member based on multiple identifiers (e.g., name, surname, nickname, address, account ID, SSN, etc.), to aggregate user data from multiple sources by this specific member, and tagging the aggregated data with a member identifier. By aggregating user data from multiple sources and tagging it with a member identifier, a newly-added record for this now existing member may be matched by cross-referencing with the existing tagged data, this improves the record management system by leveraging additional identifier information to quickly and accurately match new records to an existing member. By aggregating records for a particular member, such as through gathering all known identifiers and information about a particular user under a particular member identifier, a newly added record that may not be a sufficient match using one specific data record may still be sufficiently matched based at least in part on aggregated identifier information.

In examples, the matching process may use one or more identifier matching algorithm (e.g., fuzzy mapping) to determine if there is sufficient overlap in identifier information. If there is sufficient overlap, then the records are determined to correspond to the same person. Such a process may apply logic mapping that starts with and builds on a set of user-supplied human language rules, and may grow beyond the bounds of human capability.

By matching and aggregating data by member identifiers and automatically updating the user data for the members, the system may timely identify members that may need or benefit from specific medical service or intervention. For instance, many forms of health disease such as heart disease or diabetes can be prevented or treated if risk factors are timely identified and reduced. Thus, by timely identifying risk factors, the system may prevent or treat health disease. In addition to timely identifying risk factors, the system may also perform automatic queries to identify user data satisfying certain criteria to qualify for specific variant tests, and may automatically split the users in meaningful ways to perform AB test without leakage between groups. Such automatic queries may be set to run after hours to conserve resources during peak hours. Finally, by aggregating data, resources, such as networking resources, may also be conserved by, for example, refraining from searching through multiple databases.

The present disclosure provides an overall understanding of the principles of the structure, function, manufacture, and use of the systems and methods disclosed herein. One or more examples of the present disclosure are illustrated in the accompanying drawings. Those of ordinary skill in the art will understand that the systems and methods specifically described herein and illustrated in the accompanying drawings are non-limiting embodiments. The features illustrated or described in connection with one embodiment may be combined with the features of other embodiments, including as between systems and methods. Such modifications and variations are intended to be included within the scope of the appended claims.

Additional details are described below with reference to several example embodiments.

Figure 1:
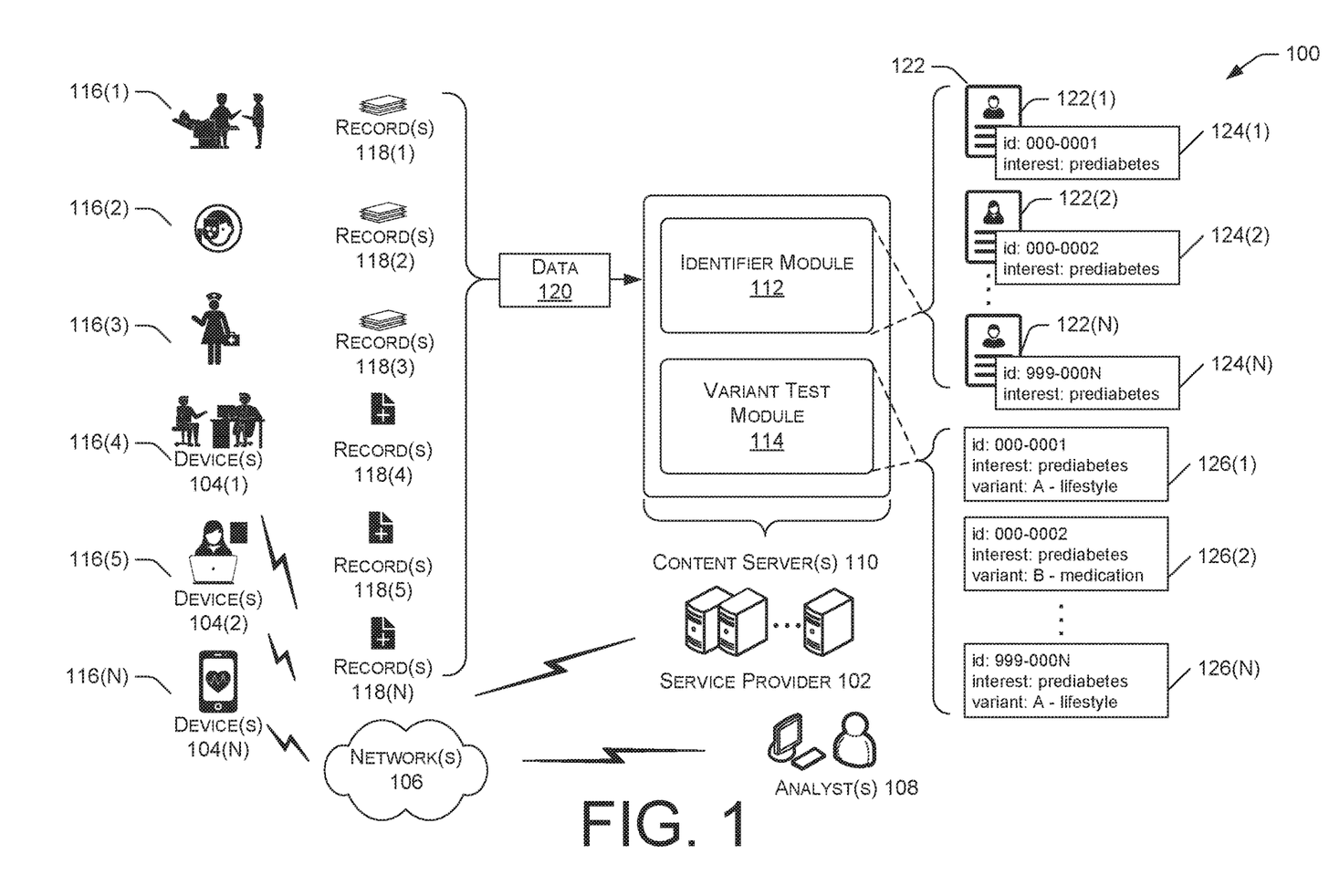
FIG. 1 illustrates a schematic diagram of an example system for relating data to identifiers for variant testing.

FIG. 1 illustrates a schematic diagram of an example system 100 for identifying related data for variant testing. The system 100 may include, for example, user(s) that utilizes device(s) 104(1)-104(N) (individually and/or collectively referred to herein with reference 104), through one or more network(s) 106, to interact with a service provider 102. In examples, the network(s) 106 may be any type of network known in the art, such as the Internet. Moreover, the service provider 102 and/or the device(s) 104 may communicatively couple to the network(s) 106 in any manner, such as by a wired or wireless connection.

The service provider 102 may be any entity, service provider network, server(s), platform, etc., that provides any type of service (e.g., medical, mental, dental, therapy, health monitors, etc.) to user(s) and that keeps records of the user(s). In examples, the service provider 102 may provide websites or apps for user(s) to view their own records. The service provider 102 may provide user portals for user(s) to upload additional data (e.g., from a fitness tracker, heartrate monitor, etc.). In various examples, the service provider may employ one or more analyst 108 (also referred to as an administrator, support personnel, etc.) to provide support for the content server(s) 110 and to create rules for the identifiers and variant tests. As shown, the service provider 102 may include one or more content server(s) 110. The content server(s) 110 may be implemented in a non-distributed computing environment or may be implemented in a distributed computing environment, possibly by running one or more modules on device(s) 104 or other remotely located devices. The content server(s) 110 may be any type of server, such as a network-accessible server.

In various examples, the service provider 102 may present the records and variant tests on behalf of the user(s), health services, and/or entities. In at least one example, the service provider 102 described herein may cause one or more user interfaces to be presented to user(s) via device(s) 104. The user interface(s) may allow the user(s) to create user accounts to access the system, among other possible uses.

The user(s) (e.g., patient, customer, member, subscriber, etc.) may interact with the service provider 102 via a site (i.e., a website), a service provider application, a self-service interface, a self-service portal, or in any other manner. The user(s) may interact with the service provider 102 to receive user data (e.g., medical record, appointment, test results, etc.) or add user data (e.g., health sensor data, user information, etc.).

In examples, the user(s) may operate corresponding device(s) 104 to perform various functions associated with the device(s) 104, which may include at least some of the operations and/or modules discussed above with respect to the service provider 102. The user(s) may operate device(s) 104 using any input/output devices including but not limited to mouse, monitors, displays, augmented glasses, keyboard, cameras, microphones, speakers, headsets, smart watches, heart monitors, and health sensors.

The network(s) 106 may enable communications between the components and/or devices shown in system 100 and/or with one or more other remote systems, as well as other networked devices. Such network(s) 106 may include one or more network interface controllers (NICs) or other types of transceiver devices to send and receive communications over the network.

For instance, each of the network(s) 106 may include a personal area network (PAN) component to enable communications over one or more short-range wireless communication channels. For instance, the PAN component may enable communications compliant with at least one of the following standards IEEE 802.15.4 (ZigBee), IEEE 802.15.1 (Bluetooth), IEEE 802.11 (WiFi), or any other PAN communication protocol. Furthermore, each of the network(s) 106 may include a wide area network (WAN) component to enable communication over a wide area network.

The analyst 108 may interact a device(s) of the content server(s) 110 or use another device(s) to interact with the content server(s) 110 through the network(s) 106. In examples, the analyst 108 may interact the device(s) to perform various functions associated with the content server(s) 110, which may include at least some of the operations and/or modules discussed above with respect to the service provider 102.

In various examples, the analyst 108 may have access to viewing the member identifier and in case of an identifier mismatch, the analyst 108 may correct the mismatch and/or retrain the matching algorithm. The analyst 108 may generate the variant tests and the different versions of the tests including determining the criteria for selecting population of interest and the criteria for measuring success. In examples, the analyst 108 may generate rules statements to automatically query the system to identify the population of interest.

In at least one configuration, the content server(s) 110 may include any components that may be used to facilitate interaction between the service provider 102 and the device(s) 104. For example, the content server(s) 110 may include the identifier module 112 and the variant test module 114.

The identifier module 112 may receive data associated with user records from various data sources and may match the data to member identifiers. The data sources for the user records may include any electronic record, fitness device data, and scanned physical records. After matching the data to a member identifier, the identifier module 112 may tag and aggregate the data by the member identifier. Based at least in part on the aggregated data for the member, the identifier module 112 may determine if there are certain health risks or interest groups for the member. For instance, if the aggregated data for a member identifies a new daily prescription and the data indicated a history of forgetting to take medication, then medicine adherence may be an interest. If the aggregated data for a member identifies elevated blood glucose level and a family history of diabetes, then diabetes may be a health risk.

The variant test module 114 may determine if there is a variant test suitable for a member based at least in part on any identified interests and user data. The variant test may include any statistical hypothesis test of any number of variant (e.g., AB test, multivariate test). In various examples, the variant test module 114 may automatically query the user database for user data meeting specific criteria for specific tests based at least in part on rules setup by the analyst 108. If the variant test module 114 identifies a number of members meeting or exceeding the minimum sample size for a specific variant test, the variant test module 114 may randomly assign the members to one version of the test. In examples, if the test is of little to no health risk (e.g., different website versions, change in service script, etc.), the analyst 108 may set the rule for the variant test module 114 to automatically apply the test. In an additional example, if the test poses health risk (e.g., intervention), the analyst 108 may set a rule for the variant test module 114 to add the member identifier to a list of qualifying subjects and notify the analyst 108.

As a non-limiting example, the example system 100 may illustrate an exemplary process of generating records from disparate data sources mapping the data to persistent member identifiers. Initially, the example data sources 116 may generate the example records 118 that are stored as example data 120. The identifier module 112 may receive the example data 120 and map the data to example member identifier 122 and the data may be aggregated into example user data 124. The identifier module 112 may identify an area of interest for the user based on the example user data 124. The variant test module 114 may identify a test for the user based at least in part on the interest and may randomly assign the example variant assignment 126 for the test.

Additionally, the example data sources 116 may generate the example records 118 associated with a user from any department or system of the service provider 102. For instance, the example data sources 116(1) may generate a dental record, or example records 118(1), following a dental exam; the example data sources 116(2) may generate retinal scans and prescription for glasses, or example records 118 (2), following a routine eye exam; the example data sources 116(3) may generate a batch of written records, or example records 118(3), from the nurse making house calls; the example data sources 116(4) may generate electronic record, or example records 118(4), from a routine office visit to the doctor's office; the example data sources 116(5) may generate user records, or example records 118(5), through the user visiting the provider's website and updating her immunization record after visiting the pharmacist; and the example data sources 116(N) may generate tracker app record, or example records 118(N), as received from a health tracker app that is associated with a member. The example records 118 that may be processed into example data 120 to transmit to the content server(s) 110.

After the example data 120 is sent to the content server(s) 110, the identifier module 112 may match and tag the example data 120 with a corresponding example member identifier 122 to form example user data 124. In the present example, the identifier module 112 has aggregated the data and assigned a health interest group of "prediabetes" to each member. Based on identifying the health interest group of "prediabetes" to the example member identifier 122, the variant test module 114 may identify a test for the members based at least in part on the interest and may randomly assign an example variant assignment 126 for the test. In the present example, the variant test module 114 may determine an intervention for members with prediabetes that includes a first version of prescribing a lifestyle change, and a second version that prescribes a medication. The variant test module 114 may assign the two variants based on a randomizing function.

Figure 2:
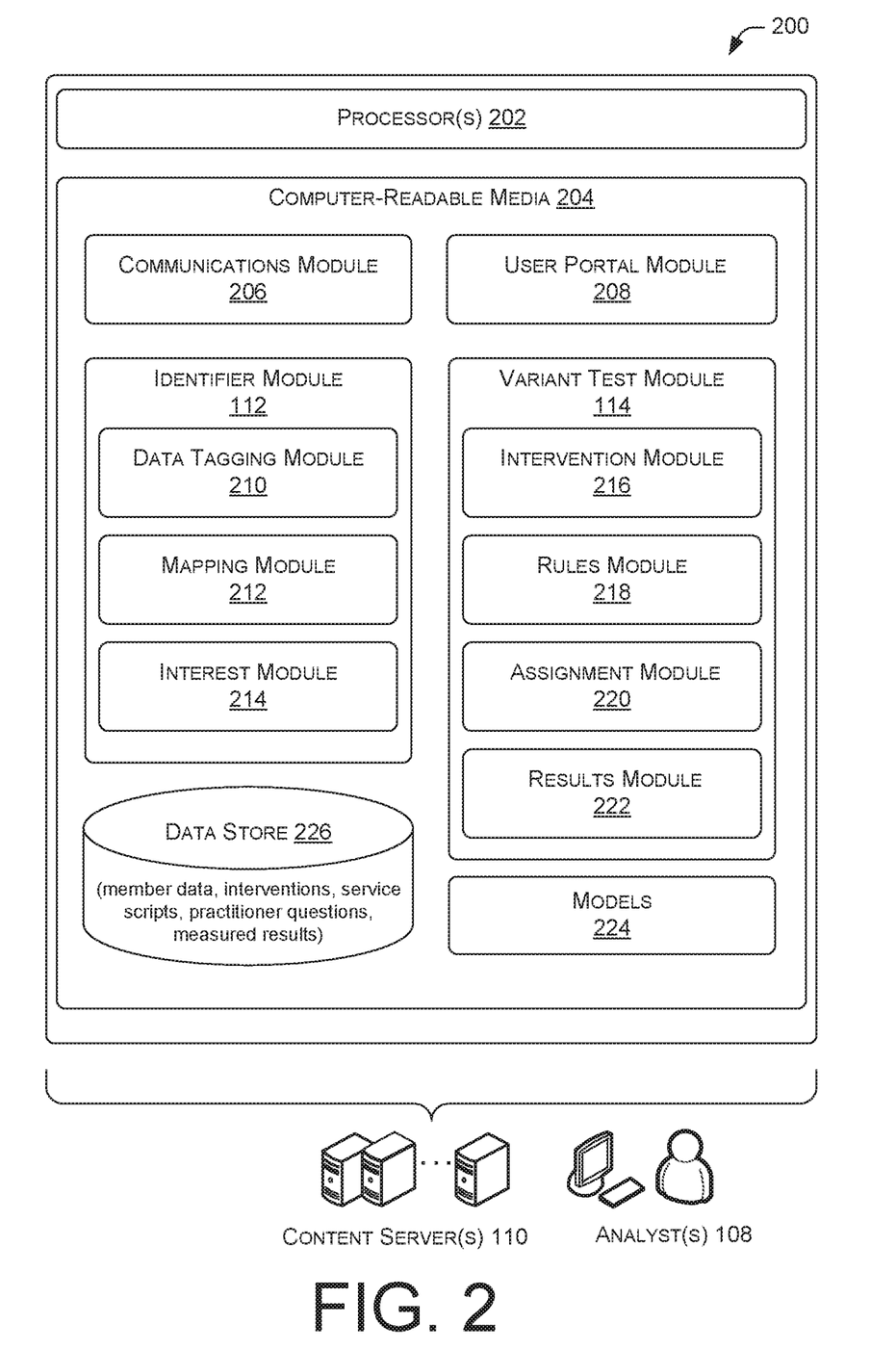
FIG. 2 illustrates a block diagram of a computing architecture of a system for relating data to identifiers for variant testing.

FIG. 2 is a block diagram of an illustrative computing architecture 200 of the content server(s) 110. The computing architecture 200 may be implemented in a distributed or non-distributed computing environment.

The computing architecture 200 may include one or more processor(s) 202 and one or more computer-readable media 204 that stores various modules, data structures, applications, programs, or other data. The computer-readable media 204 may include instructions that, when executed by the one or more processor(s) 202, cause the processors to perform the operations described herein for the system 100.

The computer-readable media 204 may include non-transitory computer-readable storage media, which may include hard drives, floppy diskettes, optical disks, CD-ROMs, DVDs, read-only memories (ROMs), random access memories (RAMs), EPROMs, EEPROMs, flash memory, magnetic or optical cards, solid-state memory devices, or other types of storage media appropriate for storing electronic instructions. In addition, in some configurations the computer-readable media 204 may include a transitory computer-readable signal (in compressed or uncompressed form). Examples of computer-readable signals, whether modulated using a carrier or not, include, but are not limited to, signals that a computer system hosting or running a computer program may be configured to access, including signals downloaded through the Internet or other networks. The order in which the operations are described is not intended to be construed as a limitation, and any number of the described operations may be combined in any order and/or in parallel to implement the process. Furthermore, the operations described below may be implemented on a single device or multiple devices.

In some configurations, the computer-readable media 204 may store the communication module 206, the user portal module 208, the identifier module 112 and associated components, the variant test module 114 and associated components, the models 224, and the data store 226, which are described in turn. The components may be stored together or in a distributed arrangement.

The communication module 206 may facilitate communication between the user(s) and the service provider 102. The communication module 206 may present various user interfaces to communicate with the user(s). In examples, the communication module 206 may present user interface allowing the user(s) to create different types of user accounts (e.g., patient, health care provider, data scientists, etc.) with the service provider 102. In at least one example, the communication module 206 may receive information associated with user(s) with a member account such as user information (e.g., name, address, age, profession, billing information, insurance, demographic, medications, allergies, etc.) and actions associated with a member account for the user(s) (e.g., visits, appointments, tests, immunization record, recent travels, etc.).

The user portal module 208 may allow the user(s) to register one or more device(s) 104, including any health trackers, heart monitors, or health sensors, with the service provider 102. The user portal module 208 may facilitate communication between registered device(s) 104 and the service provider 102. The user portal module 208 may push health sensor data associated with members for the identifier module 112 and the variant test module 114. For instance, the variant test module 114 may determine that a member needs to follow a lifestyle intervention plan, which includes daily exercise. The variant test module 114 may retrieve health tracker data to monitor the member's adherence to performing daily exercise and monitor the changes in data level.

The identifier module 112 may include the data tagging module 210, the mapping module 212, and the interest module 214. The primary goal of the identifier module 112 is to accurately identify the member identifier for new user data. To this end, the identifier module 112 may leverage its components and models 224 to build and evolve the system's identifier mapping algorithm. In various examples, the identifier module 112 and/or one or more associated components may be part of a standalone application that may be installed and stored on the user device(s) 104.

The data tagging module 210 may receive and process data associated with a member including any user records. The user records may be any type of record (e.g., dental chart, x-rays, retina scans, medical history, psych evaluation, etc.) and may be in any format (e.g., electronic documents, paper chart, photos, etc.). Initially, the data tagging module 210 may gather data associated with a user from any department or system of the service provider 102. For instance, the data tagging module 210 may receive an electronic record of a user immediately after a visit to the office or a batch of scanned record at the end of the day from a nurse, who makes house calls during the day. The data tagging module 210 may analyze the data to identify any identifier information and tag the identifier information.

The mapping module 212 may match the data to a member identifier. The mapping module 212 may perform identifier matching by receiving data tagged as identifier information and cross-referencing other tagged identifier information from other records to find overlaps or degree of similarity. If there are sufficient overlaps, or the degree of similarity meets a predetermined threshold amount of similarity, between records, those records may be aggregated by associating them with a member identifier. The mapping module 212 may determine if there is already an existing member identifier assigned to a record, if there is, the records will all be associated with the existing member identifier. If there isn't a member identifier assigned to the records, the mapping module 212 may generate a new member identifier and the records will all be associated with the new member identifier.

In examples, the mapping module 212 may train an identifier matching algorithm using training data that includes samples of customer data tagged with different identifier information corresponding to different types of identifier the data may have as training data. Once trained, the mapping module 212 may use this trained identifier matching algorithm to automatically match new records to an existing member identifier or a new member identifier and the information in the new records may also be automatically aggregated with the associated member data. That is, upon receiving new data, the mapping module 212 may automatically map the data to a member identifier and may automatically update the information model for the member.

The interest module 214 may determine if there are certain interest group for the member. After matching the data to a member identifier, the identifier module 112 may aggregate the user data based at least in part on the member identifier. The interest module 214 may determine, based at least in part on the aggregated data, that the member belongs to multiple health-related or other interest groups.

In various examples, the interest module 214 may construct and update a user information model for each member. Initially, the interest module 214 may aggregate and store user data into a user information model and determine if there is any interesting health data to flag. That is, in constructing a complete user information model, the interest module 214 may identify a certain risk pattern and may flag it for further analysis. Additionally, the interest module 214 may receive new data and may construct a new information model and determine the changes in data. Using this new information model, the interest module 214 may determine an interest group based at least in part on changes in the model. For instance, if the information model for a member identifies a new daily prescription or a need for dramatic change in lifestyle for health benefits, then medicine adherence may be an interest. If the information model for a member identifies elevated blood glucose level, then pre-diabetes may be an interest. In examples, the interest module 214 may also send alerts to an analyst or staff based at least in part on changes in a user information model that may indicate a major health concern. For instance, the analyst may create rules for the interest module 214 to notify a managing staff member if a new change in user information model puts them at risk for heart disease. Additionally, the interest module 214 may have machine learned health risks such as prescribing too much of a certain type of drugs may put a patient's health at risk and identifying such a new change in the user information model may trigger an alert for the staff to review the user record.

In examples, the interest module 214 may interact with the variant test module 114 to identify interventions or tests that may benefit the member. Initially, an analyst 108 may generate an interest group model to identify a population of interest by using basic rules for a simple variant test (e.g., change in font on web site, tracker app button, etc.) or by using a predictive algorithm to determine a probability of a health risk (e.g., likelihood that a member may be hospitalized, likelihood of a member developing diabetes, etc.). The interest module 214 may retrieve interest group models and populate these models based at least in part on the user data to determine if the user meets the criteria as belonging to the interest group.

The variant test module 114 may include the intervention module 216, the rules module 218, the assignment module 220, and the results module 222. The primary goal of the variant test module 114 is to identify a chance to enhance an outcome such as better diagnosis suspecting and improving customer experience. To this end, the variant test module 114 may leverage its components and models 224 to build and evolve the system's machine learning models 224. In various examples, the variant test module 114 and/or one or more associated components may be part of a standalone application that may be installed and stored on the user device(s) 104.

As the variant test module 114 produce more test data and results data associated with specific members, the system model may learn from such data. Accordingly, the variant test module 114 may use any portion of the user data, the test data, and the results data as input to train one or more of machine learning models 224. Machine learning generally involves processing a set of examples (called "training data") in order to train a machine learning model(s) 224. A machine learning model, once trained, is a learned mechanism that can receive new data as input and estimate or predict a result as output. For example, a trained machine learning model can comprise a classifier that is tasked with classifying unknown input (e.g., an unknown image) as one of multiple class labels (e.g., labeling the image as a cat or a dog). In the context of the present disclosure, the unknown input may include, inter alia, user data that may be indicators for health risk, and the trained machine learning model, or the system models, may be tasked with classifying the unknown input as one of multiple class labels. The class labels, in this case, may correspond to a classification of the unknown input as a type of indicator among multiple different types of indicators corresponding to different health risks.

The machine learning model(s) 224 may represent a single model or an ensemble of base-level machine learning models, and may be implemented as any type of machine learning model. For example, suitable machine learning models for use with the techniques and systems described herein include, without limitation, tree-based models, support vector machines (SVMs), kernel methods, neural networks, random forests, splines (e.g., multivariate adaptive regression splines), hidden Markov model (HMMs), Kalman filters (or enhanced Kalman filters), Bayesian networks (or Bayesian belief networks), expectation maximization, genetic algorithms, linear regression algorithms, nonlinear regression algorithms, logistic regression-based classification models, or an ensemble thereof. An "ensemble" can comprise a collection of models, as stored in the data store 226, whose outputs (classifications) are combined, such as by using weighted averaging or voting. The individual machine learning models 224 of an ensemble can differ in their expertise, and the ensemble can operate as a committee of individual machine learning models that is collectively "smarter" than any individual machine learning model of the ensemble.

The intervention module 216 may interact with the interest module 214 to determine if a member would benefit from specific intervention. The goal of the intervention module 216 is to determine, based at least in part on the information model for a member, whether the member is at risk for one or more health issues and whether early intervention may avoid the health issue. Accordingly, the intervention module 216 may use any portion of the user data and test data as input to train one or more of machine learning models 224. The trained machine learning model, or the system models, may be tasked with classifying the users as having indicators corresponding to certain health risks thus predicting an intervention for the member to avoid the health issue.

The rules module 218 may interact with the identifier module 112 to automatically apply a list of rules or criteria to query the user data. In various examples, the rules module 218 may receive instructions from the analyst 108 to automatically query the user database for members qualifying for specific tests based on rules setup by the analyst 108. In examples, if the test of little to no health risk (e.g., different website versions, change in service script, etc.), the analyst 108 may set the rule for the for the rules module 218 to automatically apply the test. In an additional example, if the test poses health risk (e.g., intervention), the analyst 108 may set a rule for the rules module 218 to automatically add the member identifier to a list of qualifying subjects and notify the analyst 108.

The assignment module 220 may select a randomizing scheme to assign a certain test or experience to a member. If the rules module 218 identifies a number of qualifying members meeting or exceeding the minimum sample size for a specific variant test, the assignment module 220 may randomly assign the members to a version of the test. The assignment module 220 may choose from one or more randomizing algorithm or scheme to split the test group. In examples, the assignment module 220 may divide a test group down based on the middle of the list or may roll on a random number generator and assign the members based on an assignment scheme (e.g., odd number assign to group A and group B for even number). For instance, if the members are added to a test group list at random, the assignment module 220 may simply assign the top half of the group to Variant A of a test and Variant B to the remaining members. In additional or alternate examples, the assignment module 220 may use a pseudo-random assignment scheme, which includes randomly assigning a particular user to a version group, storing the group assignment, and reusing the group assignment for additional tests for this particular user. For instance, a particular user may be randomly assigned to group A for a first test, and for the next test, rather than re-rolling or otherwise randomly assigning a second group assignment, this particular user may be automatically assigned to group A for the next test.

In various examples, the assignment module 220 may flag or automatically resolve a conflict during assignment. If a member is being assigned to more than one variant tests and there may be a conflict in participating in both tests, the assignment module 220 may alert an analyst 108 to resolve the conflict. For instance, a member may already be assigned to taking a medication to prevent a first disease but the system has identified the member as being a good candidate for a lifestyle change to prevent a second disease, the assignment module 220 may determine there is a conflict and flag the new assignment as a conflict for the analyst to review and resolve. In examples, the analyst 108 may include rules to automatically resolve conflicts based at least in part on priorities assigned to tests (e.g., test with immediate health risk implications may be prioritized over preventative care) or on the stage of the testing (e.g., still selecting members for test, middle of testing, etc.).

The results module 222 may interact with the user portal module 208 and the identifier module 112 to track any user data that may indicate whether the results for a variant test was successful or not. For each variant test, the criteria for selecting a population of interest and the criteria for a successful test are defined. Thus, the results module 222 may determine, based on the variant test, whether the criteria for a successful test has been met. The results module 222 may monitor and measure user data to determine the results of the variant test and store the results. For instance, as depicted in the examples in FIG. 1, if a user is assigned to "variant: A-lifestyle" for a prediabetes AB test, the results module 222 may monitor one or more diabetes-related biomarker (e.g., cholesterol level, triglycerides level, blood pressure, etc.) for the user at least at the start and completion of the test, and also monitor health devices to verify that user is exercising according to the "lifestyle" treatment plan.

In examples, the results module 222 may identify one or more data analysis algorithm or models to measure the success for a variant test and populate data for the model. The results module 222 may store and gather data from all members assigned to a particular variant test and perform data analysis on the gathered data. The results module 222 may report the results of such analysis and may allow the analyst 108 to construct additional tests based at least in part on extrapolated data. In various examples, the results module 222 may automatically push the data analysis and final test results based on predetermined deadlines set for the variant test. For instance, as described above and depicted in the examples in FIG. 1, in creating the prediabetes AB test, the analyst 108 may set duration of the test and the criteria level for success, the criteria level may include determining the amount of increase or decrease for the diabetes-related biomarker (e.g., lower blood pressure, higher levels of high-density lipoprotein (HDL) cholesterol, lower levels of triglycerides, etc.) or determining the final level is within a predetermined successful range for the diabetes-related biomarker. At the end of the duration of the test, the results module 222 may automatically generate a results report based on data analysis using the criteria for success and automatically push the generated report or a notification of the generated report to the analyst 108.

The data store 226 may store at least some data including, but not limited to, data collected from the communication module 206, the user portal module 208, the identifier module 112 and associated components, the variant test module 114 and associated components, and the models 224, including data associated with user profiles, user data, records, and images. In various examples, the identifier module 112 may store user data, member identifiers, information models, interest group data, and rules for identifier matching algorithm. In examples, the variant test module 114 may store different test variants, the rules, criteria, and models for the tests, data gathered to measure the results, and the results of the tests. In an example, the data may be automatically added via a computing device (e.g., content server(s) 110). In additional or alternative examples, at least some of the data may be stored in a cloud storage system or other data repository.

Figure 3:
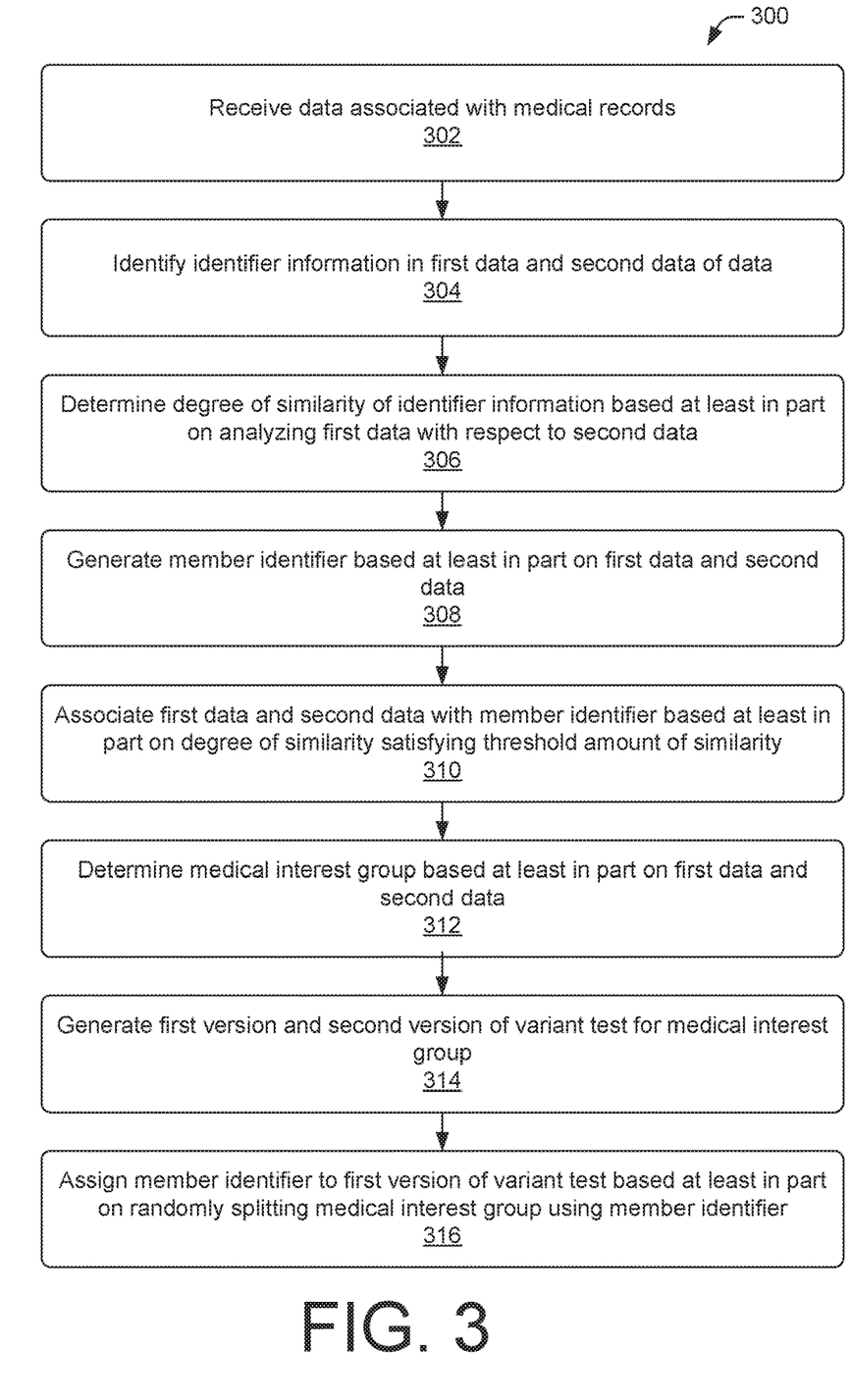
FIG. 3 illustrates a flow diagram of an example process for relating data to identifiers for variant testing.
Figure 4:
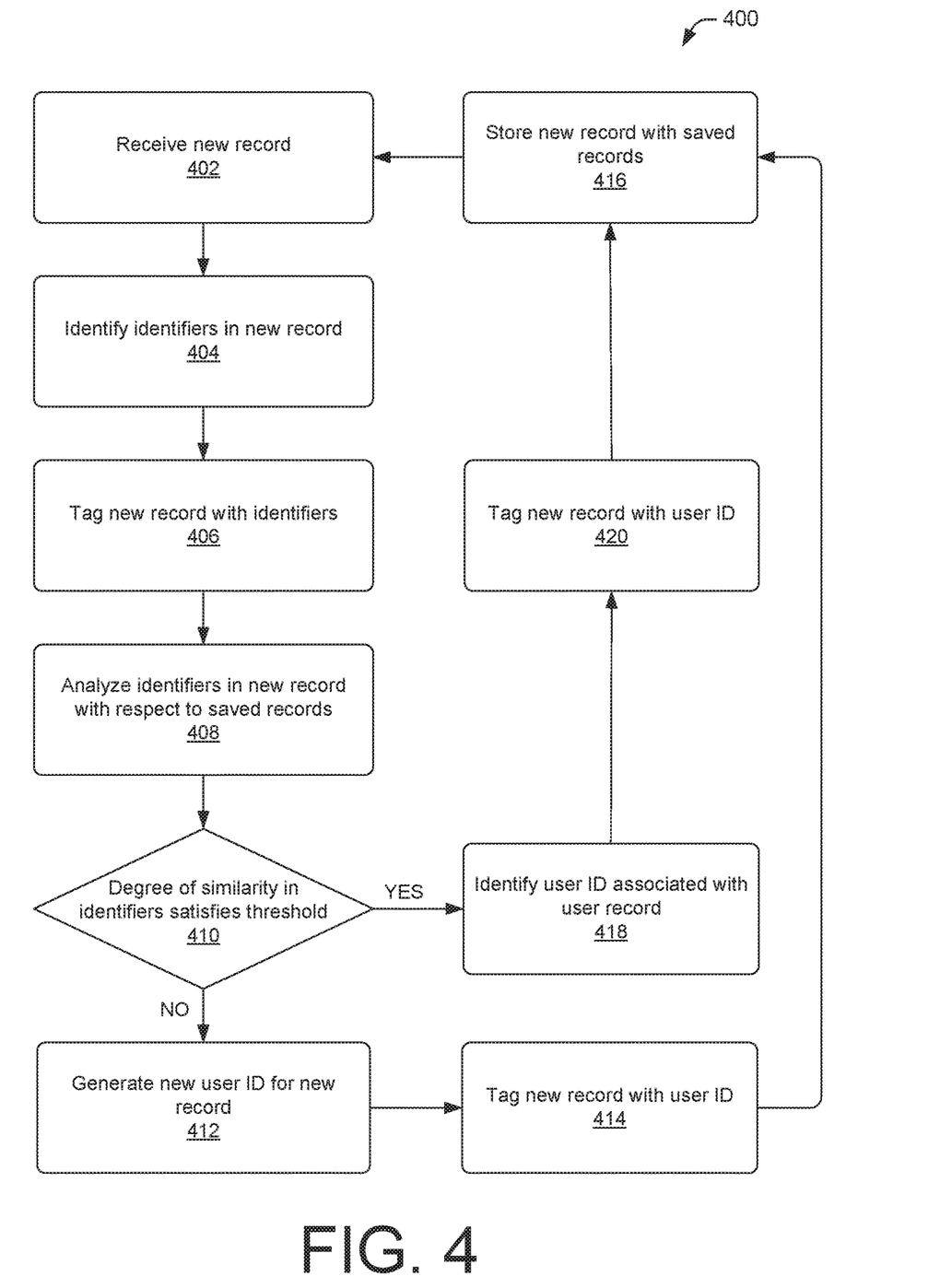
FIG. 4 illustrates a flow diagram of an example process for relating data to member identifiers.
Figure 6:
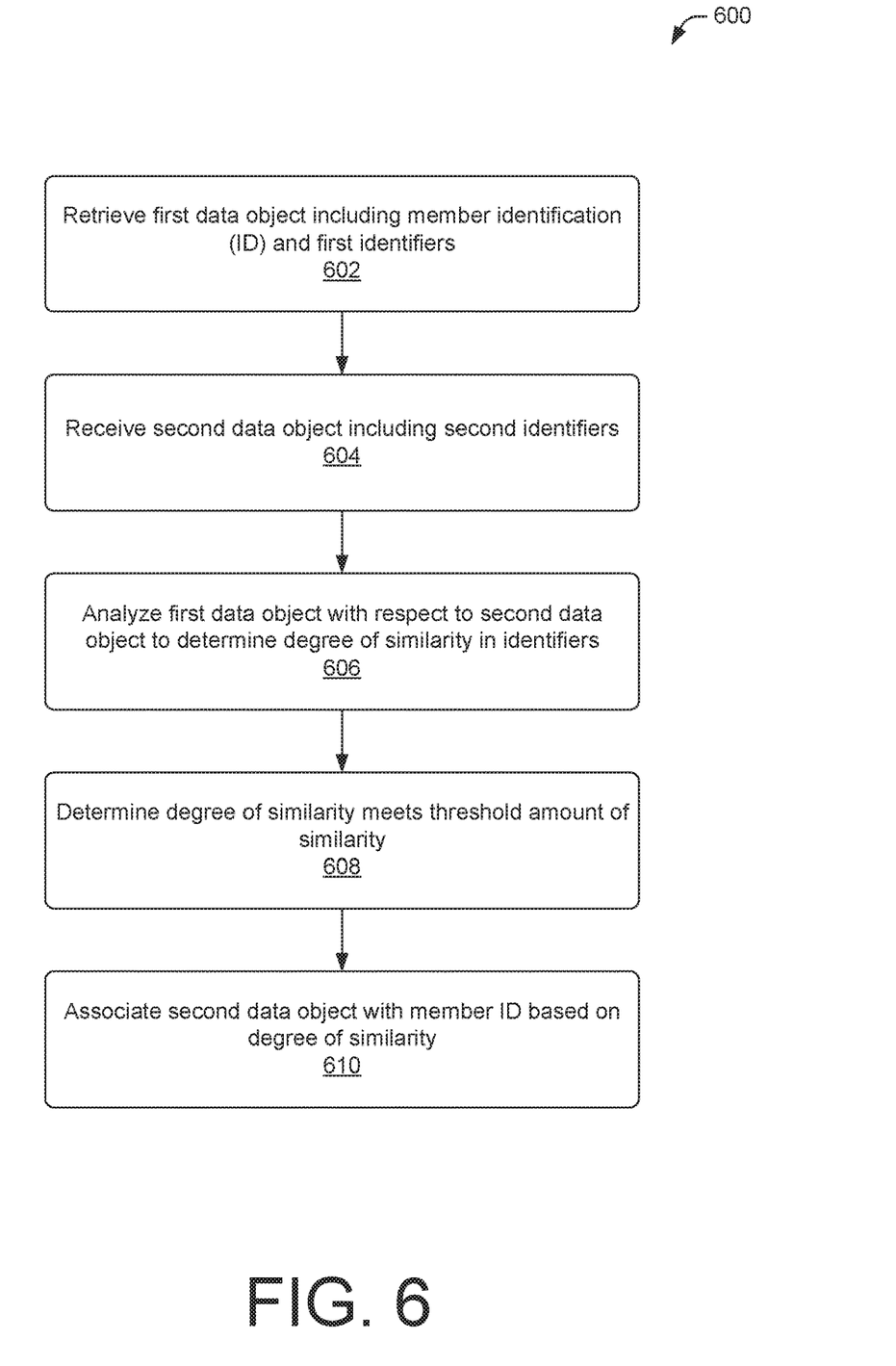
FIG. 6 illustrates a flow diagram of an example process for relating data based at least in part on identifiers.

FIGS. 3, 4, and 6 are flow diagrams of illustrative processes. The example processes are described in the context of the environment of FIG. 2, but are not limited to that environment. The processes are illustrated as a collection of blocks in a logical flow graph, which represents a sequence of operations that can be implemented in hardware, software, or a combination thereof. In the context of software, the blocks represent computer-executable instructions stored on one or more computer-readable media 204 that, when executed by one or more processor(s) 202, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the processes. The processes discussed below may be combined in any way to create derivative processes that are still within the scope of this disclosure.

FIG. 3 is a flow diagram of illustrative process 300 for identifying related data for variant testing. The order in which the operations or steps are described is not intended to be construed as a limitation, and any number of the described operations may be combined in any order and/or in parallel to implement process 300.

At block 302, the process 300 may include receiving data associated with medical records. The data may include data from different sources that have different identifier formats. The data sources for the user records may include any electronic record, fitness device data, and scanned physical records. The user records may be any type of record (e.g., dental chart, x-rays, retina scans, medical history, psych evaluation, etc.) and may be in any format (e.g., electronic documents, paper chart, photos, etc.). The data may be associated with user from any department or system of the service provider. For instance, the data associated with medical records may include an electronic record of a user transmitted immediately after a visit to the office or a batch of scanned record transmitted at the end of the day from a nurse, who makes house calls during the day.

At block 304, the process 300 may include identifying identifier information in a first data and a second data of the data. The system may analyze the data to identify any identifier information and tag the identifier information. The first data may include a first identifier format and the second data may include a second identifier format.

At block 306, the process 300 may include determining a degree of similarity of the identifier information based at least in part on analyzing the first data with respect to the second data. The system may analyze the first data with respect to the second data and cross-referencing the identifier information in the first data with respect to the identifier information in the second data to find overlaps or degree of similarity. If there are sufficient overlaps, or the degree of similarity meets a predetermined threshold amount of similarity, between the first data and the second data, the first data and the second data may be aggregated by associating them with a member identifier.

At block 308, the process 300 may include generating a member identifier based at least in part on the first data and the second data. The system may determine if there is already an existing member identifier assigned to either the first data or the second data, if there is, the first data and the second data will all be associated with the existing member identifier. If there isn't a member identifier assigned to the first data and the second data, the system may generate a new member identifier and the first data and the second data will all be associated with the new member identifier.

At block 310, the process 300 may include associating the first data and the second data with the member identifier based at least in part on the degree of similarity satisfying a threshold amount of similarity. As previously discussed, if there are sufficient overlaps, or the degree of similarity meets a predetermined threshold amount of similarity, between the first data and the second data, the first data and the second data may be aggregated by associating them with a member identifier.

At block 312, the process 300 may include determining a medical interest group based at least in part on first data and the second data. The system may identify a medical interest group that may benefit the member. Initially, an analyst may generate a medical interest group model to identify a population of interest by using basic rules for a simple variant test (e.g., change in font on web site, tracker app button, etc.) or by using a predictive algorithm to determine a probability of a health risk (e.g., likelihood that a member may be hospitalized, likelihood of a member developing diabetes, etc.). The system may retrieve interest group models and populate these models based at least in part on the first data and the second data to determine if the user meets the criteria as belonging to the interest group.

At block 314, the process 300 may include generating a first version and a second version of a variant test for the medical interest group. The analyst may determine a set of criteria to identify a population of interest for a medical interest group and the criteria for measuring the success. According the analyst may create different versions of the test to generate data for measuring success. In examples, the system may generate different versions of the test.

At block 316, the process 300 may include assigning the member identifier to the first version of the variant test based at least in part on randomly splitting the medical interest group using the member identifier. The system may select a randomizing scheme to assign a certain test or experience to the member identifier. The system may choose from one or more randomizing algorithm or scheme to split a test group. In examples, the system may divide a test group down based on the middle of the list or may roll on a random number generator and assign the members based on an assignment scheme (e.g., odd number assign to first version and second version for even number). For instance, if the members are added to the medical interest group at random, the system may simply assign the top half of the group to first version of the variant test and the second version to the remaining members of the variant test.

FIG. 4 illustrates a flow diagram of an example process 400 for identifying related data and determining whether to generate a new member identifier. The order in which the operations or steps are described is not intended to be construed as a limitation, and any number of the described operations may be combined in any order and/or in parallel to implement process 400.

At block 402, the process 400 may include receiving a new record. The new record may include record from different sources that have different identifier formats. The data sources for the new record may include any electronic record, fitness device data, and scanned physical records. The new record may be any type of record (e.g., dental chart, x-rays, retina scans, medical history, psych evaluation, etc.) and may be in any format (e.g., electronic documents, paper chart, photos, etc.). The new record may be associated with user from any department or system of the service provider. For instance, the new record may include an electronic record of a user transmitted immediately after a visit to the office or a batch of scanned record transmitted at the end of the day from a nurse, who makes house calls during the day.

At block 404, the process 400 may include identifying identifiers in the new record. The system may analyze the new record to identify any identifier information and tag the identifier information.

At block 406, the process 400 may include tagging the new record with the identifiers.

At block 408, the process 400 may include analyzing the identifiers in the new record with respect to the saved records. The system may analyze identifiers in the new record with respect to the saved records and cross-referencing the identifier information in the new record with respect to the identifier information in the saved records to find overlaps or degree of similarity.

At block 410, the process 400 may include determining if the degree of similarity in identifiers satisfies a threshold. The system may analyze identifiers in the new record with respect to the saved records and cross-referencing the identifier information in the new record with respect to the identifier information in the saved records to find a degree of similarity between the records.

At block 412, the process 400 may include generating a new user ID for the new record. If the system determines the new record does not overlap any record in the saved records, or the degree of similarity is below a predetermined threshold amount of similarity, between the identifiers in the new record and the saved records, the system may determine this new record does not belong to an existing member. Based at least in part on the new record not overlapping a saved record, the system may generate a new user identifier for the new record.

At block 414, the process 400 may include tagging the new record with new user ID. The new record may be associated with the new user ID.

At block 416, the process 400 may include storing the new record with the saved records. The new record may be stored with the saved records.

At block 418, the process 400 may include identifying the user ID associated with the user record. If there are sufficient overlaps, or the degree of similarity meets a predetermined threshold amount of similarity, between the identifiers in the new record and a user record of the saved records, the new record and the user record may be aggregated by associating them by the user ID for the user record. The system may analyze the user record to determine the user ID associated with it.

At block 420, the process 400 may include tagging the new record with the user ID. The new record and the user record may be aggregated by associating them with the user ID for the user record. The process may store move to block 416 to store the new record with the saved records.

Figure 5:
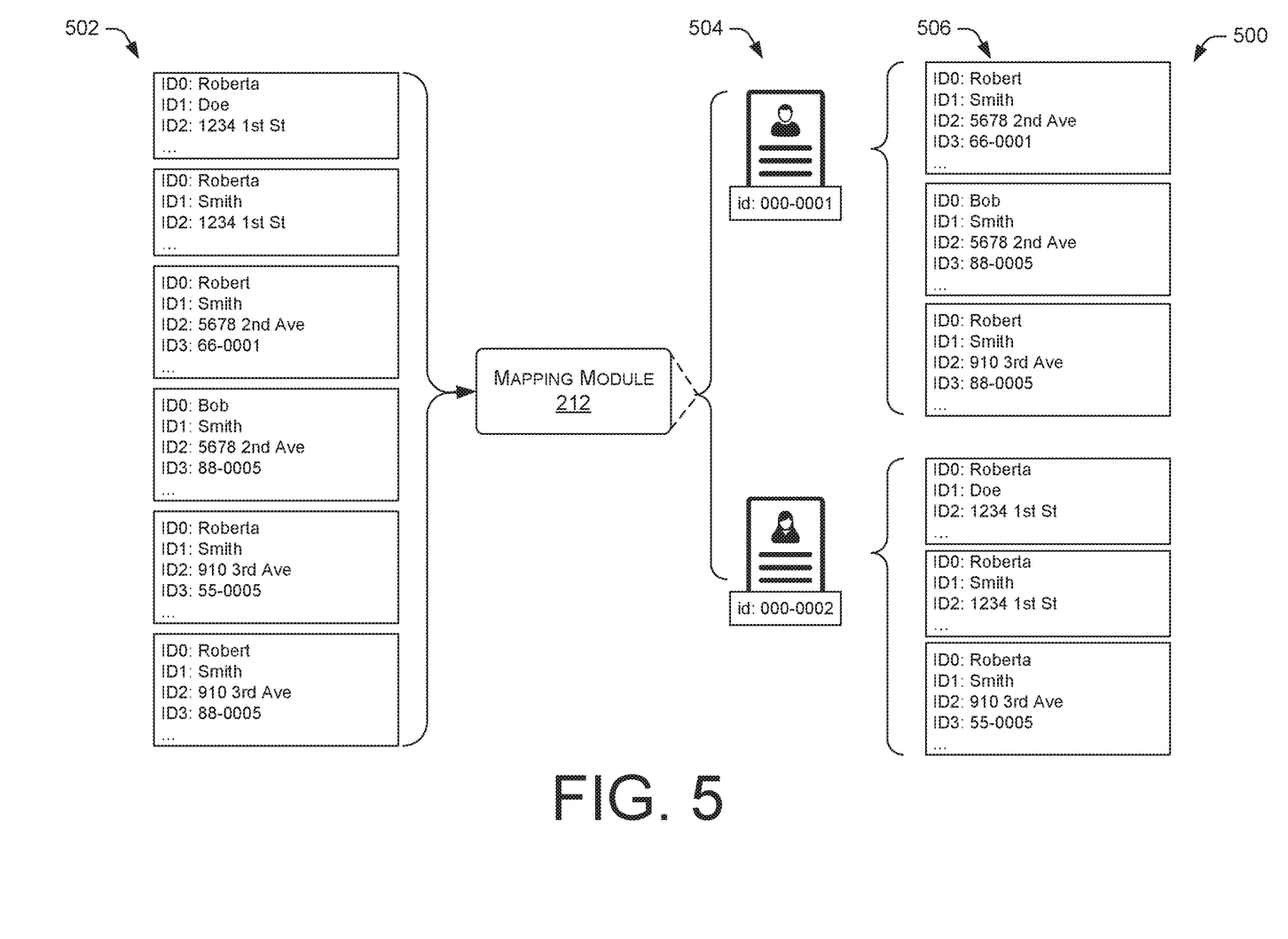
FIG. 5 illustrates a schematic diagram of an example process for relating data based at least in part on identifier types and identifier information.

FIG. 5 illustrates a schematic diagram of an example system 500 of a process for identifying related data based at least in part on the types of identifiers and the identifier information on the records. The mapping module 212 may receive example tagged data 502 may match the data to an example member ID 504 and store the example matched data 506.

As a non-limiting example, the mapping module 212 may receive the example tagged data 502. The example tagged data 502 may include data from different sources that have different identifier formats such that it may use certain identifier types (e.g., name, surname, address, user identifier (ID), SSN, etc.). In the example tagged data 502, a first identifier format may identify a member by name, surname, and address; while a second identifier format may identify a member by name, surname, address, and user ID. The mapping module 212 may perform identifier matching by receiving the example tagged data 502 and cross-referencing the data within the record to find overlaps or degree of similarity. The mapping module 212 may determine there are similarity between the record and group them as the example matched data 506. Although the information for the member may have changed, such as change in surname or using a nickname, the mapping module 212 may still identify a match based at least in part on sufficient overlap of the remaining information. If there isn't a member identifier assigned to the example matched data 506, the mapping module 212 may generate a new member identifier and the records will all be associated with the new member identifier otherwise, it will be assigned to an existing member identifier. The mapping module 212 may associate the example matched data 506 to a corresponding member ID from the example member ID 504.

FIG. 6 illustrates a flow diagram of an example process 600 for identifying related data and determine an interest based at least in part on the aggregated data. The order in which the operations or steps are described is not intended to be construed as a limitation, and any number of the described operations may be combined in any order and/or in parallel to implement process 600.

At block 602, the process 600 may include retrieving a first data object including a member identification (ID) and first identifiers. The first data object may include data from a particular data source that have a particular identifier format. The data source for the first data object may include any electronic record, fitness device data, and scanned physical records. The first data object may be processed by the system and may be assigned a member ID.

At block 604, the process 600 may include receiving a second data object including second identifiers. The second data object may include data from a second data source that have a second identifier format. The second data source for the second data object may include any electronic record, fitness device data, and scanned physical records.

At block 606, the process 600 may include analyzing the first data object with respect to the second data object to determine a degree of similarity in identifiers. The system may analyze the first data object with respect to the second data object and cross-referencing the identifier information in the first data object with respect to the identifier information in the second data object to find overlaps or degree of similarity.

At block 608, the process 600 may include determining that the degree of similarity meets a threshold amount of similarity. If there are sufficient overlaps, or the degree of similarity meets a predetermined threshold amount of similarity, between the first data object and the second data object, the first data object and the second data object may be aggregated by associating them with a member identifier.

At block 610, the process 600 may include associating the second data object with the member ID based at least in part on the degree of similarity. By associating the second data object with the same member ID as the first data object, the data from both data objects may be aggregated.

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A method, comprising:
   assigning, by one or more processors, a first patient to a first version of a variant test and a second patient to a second version of the variant test, the first version different from the second version;
   training, by the one or more processors, a machine-learned model to determine a degree of similarity between identification information included in different records from different sources and having different formats, wherein the machine-learned model is trained to output a higher degree of similarity between different records that are associated with a same person and output a lower degree of similarity between different records that are associated with different people;
   receiving, by the one or more processors, a first medical record from a first source, the first medical record including first identification information associated with the first patient, wherein the first identification information is in a first format that utilizes a first group of patient-specific identifiers for identifying the first patient;
   receiving, by the one or more processors, a second medical record from a second source, the second medical record including second identification information associated with the second patient, wherein the second identification information is in a second format that utilizes a second group of the patient-specific identifiers for identifying the second patient;
   inputting, by the one or more processors, the first medical record and the second medical record into the machine-learned model;
   receiving, from the machine-learned model, an output indicating a high degree of similarity between the first identification information and the second identification information, wherein the high degree of similarity is based at least in part on a number of the patient-specific identifiers from the first group that overlap with the second group;
   determining, based at least in part on the high degree of similarity being greater than a threshold, that the first medical record and the second medical record correspond with a same patient;
   generating, by the one or more processors, a user identifier (ID) for identifying the same patient;
   associating, by the one or more processors, the first medical record and the second medical record with the user ID;
   determining, by the one or more processors and based at least in part on the first medical record and the second medical record corresponding with the same patient, that the same patient is assigned to the first version and the second version of the variant test;
   determining, by the one or more processors, that the first version of the variant test is a suitable version of the variant test to assign the user ID to based at least in part on a combination of the first medical record and the second medical record;

assigning, by the one or more processors, the user ID to the first version of the variant test, wherein assigning the user ID to the first version of the variant test prevents the second version of the variant test from being assigned to the same patient during a same period of time as the first version of the variant test; and storing, by the one or more processors, an association between the user ID and each of the first medical record and the second medical record.

2. The method of claim 1, wherein the patient-specific identifiers include one or more of a name of the first patient, a nickname of the first patient, a surname of the first patient, a previous last name of the first patient, a date of birth of the first patient, an address of the first patient, an account identifier of the first patient, or a social security number of the first patient.

3. The method of claim 1, further comprising aggregating, as aggregated data, the first medical record and the second medical record, wherein storing the association between the user ID and each of the first medical record and the second medical record comprises storing the association between the user ID and the aggregated data.

4. The method of claim 3, further comprising determining a medical interest group for associating the user ID with based at least in part on the aggregated data satisfying criteria of the medical interest group, and wherein assigning the user ID to the first version of the variant test is based at least in part on randomly splitting the medical interest group.

5. The method of claim 4, further comprising:
determining a second medical interest group based at least in part on the aggregated data satisfying second criteria of the second medical interest group; and
associating the user ID with the second medical interest group.

6. The method of claim 5, further comprising:
identifying a first variant test associated with the medical interest group;
identifying a second variant test associated with the second medical interest group; and
assigning the user ID to the first variant test and the second variant test based at least in part on satisfying a conflict check.

7. A system comprising:
one or more processors; and
non-transitory computer-readable media storing first computer-executable instructions that, when executed by the one or more processors, cause the one or more processors to perform operations comprising:
assigning a first patient to a first version of a variant test and a second patient to a second version of the variant test, the first version different from the second version;
training a machine-learned model to determine a degree of similarity between different identification information included in different records from different sources, wherein the machine-learned model is trained to output a higher degree of similarity between different records that are associated with a same person and output a lower degree of similarity between different records that are associated with different people;
receiving a first medical record from a first source, the first medical record including first identification information associated with the first patient, wherein the first identification information is in a first format that utilizes a first group of patient-specific identifiers for identifying the first patient;

receiving a second medical record from a second source, the second medical record including second identification information associated with the second patient, wherein the second identification information is in a second format that utilizes a second group of patient-specific identifiers for identifying the second patient;
inputting the first medical record and the second medical record into the machine-learned model;
receiving, from the machine-learned model, an output indicating a high degree of similarity between the first identification information and the second identification information, wherein the high degree of similarity is based at least in part on a number of the patient-specific identifiers from the first group that overlap with the second group;
determining, based at least in part on the high degree of similarity being greater than a threshold, that the first medical record and the second medical record correspond with a same patient;
generating, by the one or more processors, a user identifier (ID) for identifying the same patient;
associating the first medical record and the second medical record with the user ID;
determining, based at least in part on the first medical record and the second medical record corresponding with the same patient, that the same patient is assigned to the first version and the second version of the variant test;
determining that the first version of the variant test is a suitable version of the variant test to assign the user ID to based at least in part on a combination of the first medical record and the second medical record; and
assigning the user ID to the first version of the variant test, wherein assigning the user ID to the first version of the variant test prevents the second version of the variant test from being assigned to the same patient during a same period of time as the first version of the variant test.

8. The system of claim 7, the operations further comprising:
determining that information included in at least one of the first medical record or the second medical record meets one or more selection criteria for a medical interest group; and
assigning the user ID to the first version based at least in part on randomly splitting the medical interest group using the user ID.

9. The system of claim 7, wherein the operations further comprise:
presenting the first version of the variant test to the same patient based at least in part on the assigning the user ID to the first version of the variant test;
receiving test data associated with the first version of the variant test;
aggregating the test data with group data associated with the variant test; and
performing data analysis on the group data to determine results for the variant test.

10. The method of claim 1, wherein the first identification information and the second identification information each include a same patient-specific identifier associated with the same patient, the same patient-specific identifier comprising at least one of a social security number associated with the same patient, an address associated with the same patient, or a name associated with the same patient.

11. The system of claim 7, wherein the first format and the second format are different formats such that the first format includes a first patient-specific identifier that is different than a second patient-specific identifier included in the second format.

12. The system of claim 7, wherein the first identification information and the second identification information each include a same patient-specific identifier associated with the same patient, the same patient-specific identifier comprising at least one of a social security number associated with the same patient, an address associated with the same patient, or a name associated with the same patient.

13. One or more non-transitory computer-readable media storing instructions that, when executed, cause one or more processors to perform operations comprising:

assigning a first patient to a first version of a variant test and a second patient to a second version of the variant test, the first version different from the second version;

training a machine-learned model to determine a degree of similarity that is indicative of whether two or more sources of identification information correspond with a same person, wherein the machine-learned model is trained to output a higher degree of similarity for two or more sources of identification information that are associated with the same person and output a lower degree of similarity for two or more sources of identification information that are associated with different people;

receiving a first medical record from a first source, the first medical record including first identification information associated with the first patient, wherein the first identification information is in a first format that utilizes a first subset of patient-specific identifiers for identifying the first patient;

receiving a second medical record from a second source, the second medical record including second identification information associated with the second patient, wherein the second identification information is in a second format that utilizes a second subset of the patient-specific identifiers to identify the second patient;

determining, using the machine-learned model, a high degree of similarity between the first identification information and the second identification information, wherein the high degree of similarity is based at least in part on a number of the patient-specific identifiers correlated between the first subset and the second subset;

determining, based at least in part on the high degree of similarity being greater than a threshold, that the first medical record and the second medical record correspond with a same patient;

generating, by the one or more processors, a user identifier (ID) for identifying the same patient;

determining, by the one or more processors and based at least in part on determining that the first medical record and the second medical record correspond with the same patient, that the same patient is assigned to the first version and the second version of the variant test;

determining, by the one or more processors, that the first version of the variant test is a suitable version of the variant test to assign the user ID to based at least in part on a combination of the first medical record and the second medical record; and assigning the user ID to the first version of the variant test, wherein determining that the first medical record and the second medical record are associated with the same patient prevents the same patient from being assigned to the second version of the variant test during a same period of time as being assigned to the first version of the variant test.

14. The one or more non-transitory computer-readable media of claim 13, the operations further comprising:

aggregating, as aggregated data, the first medical record and the second medical record; and storing the aggregated data.

15. The one or more non-transitory computer-readable media of claim 13, the operations further comprising:

determining a medical interest group for the same patient based at least in part on the first medical record and the second medical record being indicative of a probability of a health risk of the same patient;

generating the first version of the variant test for the medical interest group that is different from the second version of the variant test; and assigning the user identifier (ID) associated with the same patient to the first version of the variant test.

16. The one or more non-transitory computer-readable media of claim 15, wherein determining the medical interest group further comprises:

determining that the same patient satisfies first criteria associated with the medical interest group;

determining that the same patient satisfies second criteria associated with a second medical interest group; and determining that the medical interest group has a higher priority than the second medical interest group.

17. The one or more non-transitory computer-readable media of claim 13, wherein the first identification information and the second identification information each include a same patient-specific identifier associated with the same patient, the same patient-specific identifier comprising at least one of a social security number associated with the same patient, an address associated with the same patient, or a name associated with the same patient.

18. The method of claim 1, wherein the high degree of similarity is based at least in part on a social security number associated with the same patient being included in both of the first group and the second group.

19. The method of claim 1, wherein the machine-learned model utilizes a fuzzy mapping algorithm to determine whether high degrees of similarity exist between the different records.

* * * * *